United States Patent [19]

Hollrah

[11] Patent Number: 4,766,890
[45] Date of Patent: Aug. 30, 1988

[54] CAST WITH SPACED-APART RIBS

[76] Inventor: Scott Hollrah, 14909 Caenen La., Olathe, Kans. 66062

[21] Appl. No.: 839

[22] Filed: Jan. 6, 1987

[51] Int. Cl.$^4$ ............................................. A61F 5/04
[52] U.S. Cl. ................................. 128/89 R; 128/87 R
[58] Field of Search .................... 128/87 R, 89 R, 90, 128/91 R, 80 R, 83, 82, 85, 77, 133

[56] References Cited

U.S. PATENT DOCUMENTS

| | | | |
|---|---|---|---|
| 67,493 | 8/1867 | Burch . | |
| 594,076 | 11/1896 | Gardiner | 128/87 R |
| 739,634 | 9/1903 | Allen . | |
| 1,635,230 | 7/1927 | Spicer | 128/133 |
| 2,785,672 | 3/1957 | Napoli | 128/87 |
| 2,984,239 | 5/1961 | Taylor | 128/87 |
| 3,389,700 | 6/1968 | Whyte | 128/91 R |
| 3,976,062 | 8/1976 | Cox | 128/89 R X |
| 4,143,653 | 3/1979 | Wichman | 128/89 R X |
| 4,414,965 | 11/1983 | Mauldin et al. | 128/87 |
| 4,489,716 | 12/1984 | Blackwood et al. | 128/87 |
| 4,530,352 | 7/1985 | Holloway | 128/89 R |
| 4,662,364 | 5/1987 | Viegas et al. | 128/87 R |

Primary Examiner—Robert A. Hafer
Assistant Examiner—Michael Brown
Attorney, Agent, or Firm—D. A. N. Chase

[57] ABSTRACT

An improved cast comprising an array of spaced-apart support ribs for immobilizing a fracture site. The ribs are held in place by first and second straps and casting tape encircling the rib grid. The rib array includes laterally aligned tape fasteners which provide visual indicia for wrapping the casting tape about the rib array and hold the casting tape in place during hardening. The rib array provides a lightweight cast which allows light and air to impinge upon the fracture site so as to enhance healing and preclude moisture-induced cast deterioration and skin irritation.

10 Claims, 2 Drawing Sheets

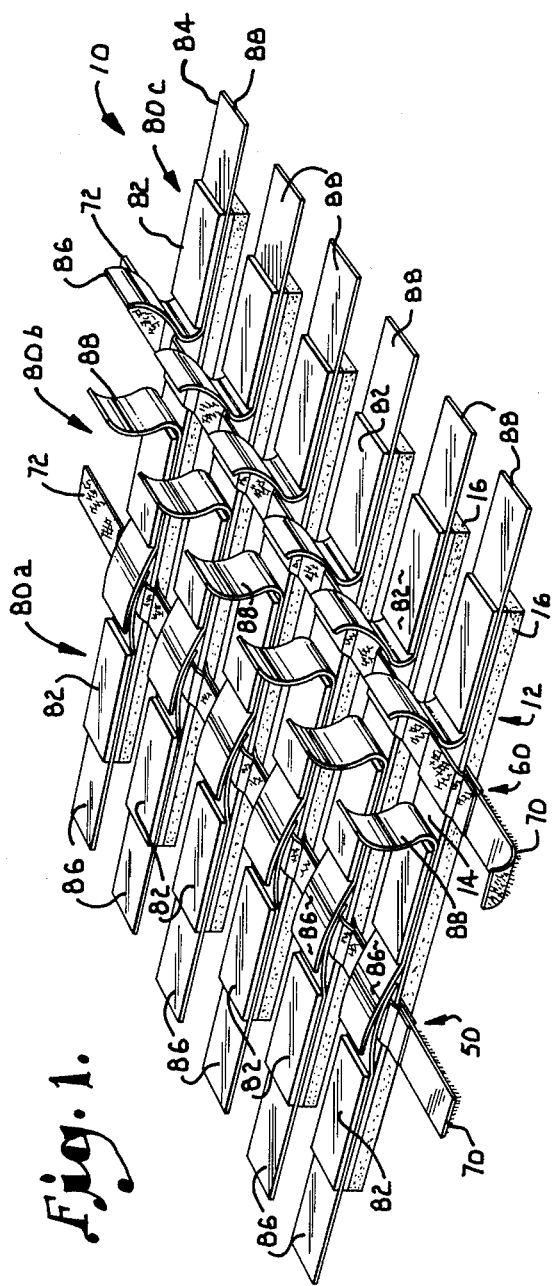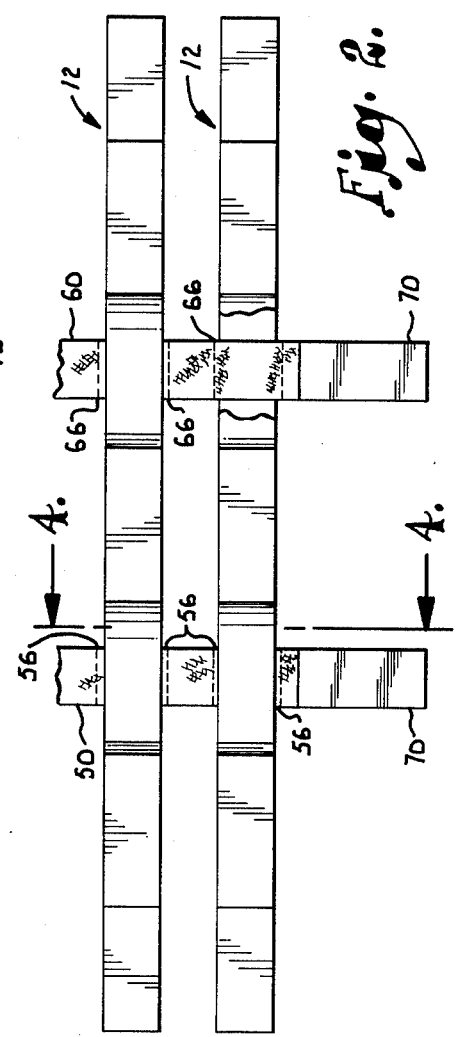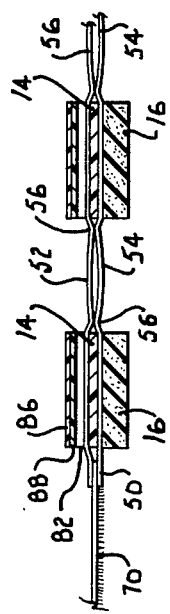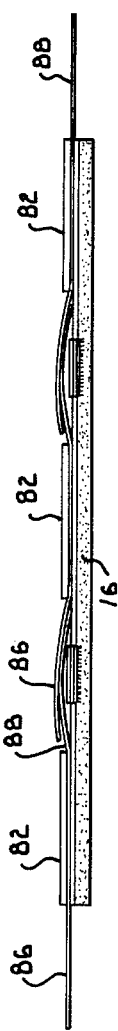

CAST WITH SPACED-APART RIBS

BACKGROUND OF THE INVENTION

This invention relates to an improved cast design for limb immobilization and more particularly to a lightweight, latticed cast which presents a support rib array so as to delimit skin irritation and resist moisture and pressure disintegration.

Conventional casts utilize a rigid plaster dressing(s) so as to immobilize the broken or fractured bone to enhance healing. Such casts include the use of a stockinet material which encircles the fracture site. Cotton padding may also be used for softness. Plaster and plaster tape are then applied about the material and, once dried, immobilize the fracture site. (A water-activated, polyurethane tape may be substituted for the plaster tape).

The conventional plaster cast is subject to disintegration, inclusive of cracking and chipping, over time. These conventional casts are subject to deterioration from moisture. Also, as fresh air and light cannot impinge on the covered fracture site, skin irritations, or rashes, may result. The relatively heavy plaster cast can also abrade the underlying skin and impede the normal performances of the wearer's daily activities.

In response thereto, I have invented an improved cast which utilizes a plurality of longitudinally spaced-apart ribs to present a rib grid/array for encircling the fracture site. The ribs are preferably flexible and foam padded so as to longitudinally trace the configuration of the fracture site without abrasion/irritation to the underlying skin. First and second straps are traversely secured to the ribs to initially position the rib grid/latticed array. These straps initially maintain the rib array in place about the fracture site. A preferably polyurethane, water-activated tape (e.g., Deltalight ®) is wound about the exterior of the ribs at selected positions as presented by tape fasteners. The dried tape, once rigid, maintains the rib grid in its immobilizing position about the fracture site.

A lightweight cast is thus presented which relieves the wearer's pain; prevents undesirable stresses and strains from acting on the fracture site and does not shift or otherwise displace relative to the fracture site. I have found that this cast is easily applied; is more resistant to chipping; does not interfere with radiological clarity; has a greater resistance to moisture and pressure deterioration and allows light and air to impinge upon the fracture site which delimits the degradation of the skin of the user.

Accordingly, it is an object of this invention to provide an improved cast for immobilizing bone fractures during healing.

Still another object of this invention is to provide an improved cast, as aforesaid, which utilizes a support rib array so as to be relatively lightweight, durable in construction, easily applied and more convenient to wear than conventional casts heretofore employed.

Another object of this invention is to provide an improved cast, as aforesaid, which positively delimits undesirable movement of the fracture site.

A further object of this invention is to provide an improved cast, as aforesaid, which reduces the interference of the cast with the wearer's daily activities.

Still another object of this invention is to provide an improved cast, as aforesaid, which avoids abrasion of the underlying skin of the fracture site.

A more particular object of this invention is to provide an improved, washable cast, as aforesaid, which allows air and light to impinge upon the fracture site and is thus relatively impervious to moisture impinging thereon.

Another particular object of this invention is to provide an improved cast, as aforesaid, which distributes the pressure of the cast along the fracture site so as to enhance blood circulation through the fracture site.

A more particular object of this invention is to provide an improved cast, as aforesaid, which allows physical inspection and access to the fracture site and is relatively nonsensitive to tissue swelling in the fracture site.

Other objects and advantages of this invention will become apparent from this specification taken in connection with the accompanying drawings, wherein is set forth by way of illustration and example, an embodiment of this invention.

BRIEF DESCRIPTION OF THE DRAWINGS

FIG. 1 is a perspective view showing the improved cast in an initial, horizontal position so as to present a rib grid/latticed array with selected flaps of the tape fasteners being raised to assist in illustration;

FIG. 2 is a fragmentary plan view illustrating the relationship among first and second support ribs, strap fasteners and tape fasteners with a flap of a tape fastener being broken away to illustrate a strap fastener traversing a rib;

FIG. 3 is a side view of the structure in FIG. 2 and illustrates the relationship of a rib with the strap fasteners and tape fasteners;

FIG. 4 is a sectional view, taken along line 4—4 in FIG. 2, and illustrates the construction of the support rib and the method of attaching the strap fasteners thereto;

DESCRIPTION OF THE PREFERRED EMBODIMENT

Figure 5:
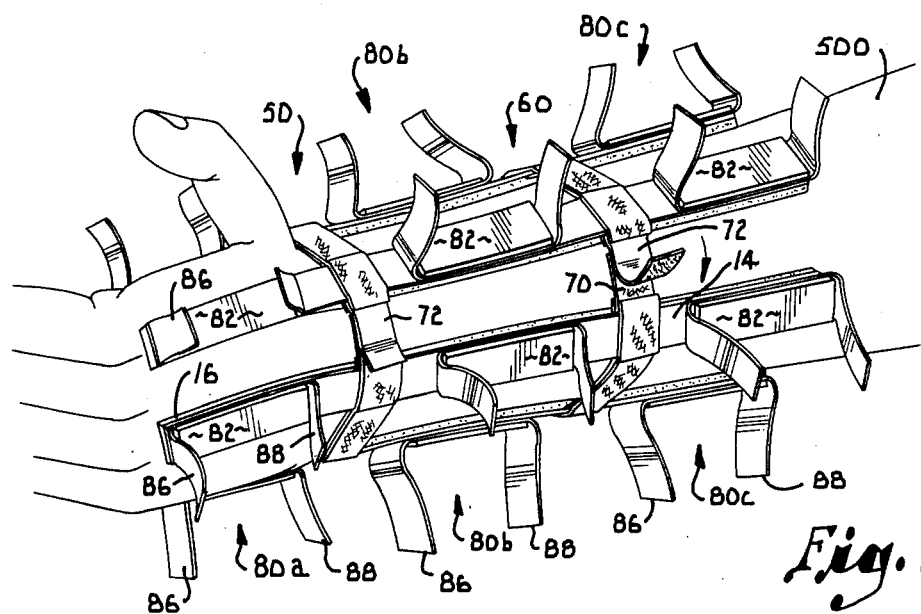
FIG. 5 is a perspective view illustrating the initial position of the improved cast about the forearm so as to treat a fractured ulna (distal/one third) as initially held in place by the first and second strap fasteners.

Turning more particularly to the drawings, my improved cast 10 is illustrated for use on the forearm 500 of the wearer in connection with a distal fracture of the ulna. It is understood that my cast 10, as disclosed herein, is adaptable for use on other fracture sites.

FIG. 1 illustrates the improved cast 10 as presenting a rib grid or latticed array prior to use. It is understood that the rib grid can be non-specific as to dimensions and later modified according to the dimensions of the fracture site to be immobilized.

As such, the latticed framework comprises a plurality of elongated ribs 12, preferably made of a flexible material, so as to longitudinally trace and conform to the forearm configuration of the fracture site. Each rib 12 generally comprises an elongated face strip 14 with an underlying foam rubber pad 16 for contacting the skin of the wearer. I prefer the use of foam rubber 16, or other closed cell compressible material as the skin contacting material rather than cotton or the like as cotton may trap moisture which can lead to the growth of fungi or bacteria.

First and second flexible straps 50, 60 are traversely connected to the plurality of ribs 12. My now preferred method of attachment is to use straps of a double-ply construction 52, 54 and 62, 64 which traverse above and below the face strip 14. The plies are sewn together adjacent the opposed sides of each face strip as shown at 56 and 66 so as to preclude undesirable shifting of the straps 50, 60 relative to the rib array 12. The opposed ends of each strap 50, 60 are provided with complementary Velcro ® mating elements 70, 72. The underlying skin contacting pad 16 covers the portion of the respective lower plies 54, 64 which traverses the inferior side of each face strip 14.

Longitudinally spaced along the face strip 14 of each rib 12 are a plurality of raised tape fasteners 80 designated as 80a, 80b, 80c. Each fastener 80a, 80b, 80c is further laterally aligned among the plurality of ribs 12. Each fastener 80 includes a raised base 82 adhesively attached to the exterior side of the face strip 14 with a plastic strip 84 therebetween. Upon affixation, first 86 and second 88 tabs/flaps extend from opposite sides of each base 82. These flaps cooperate with the base 82 so as to present a zone of overlay to the user for the casting tape in a manner to be subsequently described.

In use, the grid 10 is positioned about the forearm so as to encircle the fracture site as shown for this particular application in FIG. 5. The length of the ribs 12 is such that it would approximate the length of a conventionally applied plaster cast. For this particular application, the laterally aligned tape fasteners 80a are placed distally adjacent the thumb 502 of the wearer as shown in FIG. 6.

Upon initial placement, as shown in FIG. 5, the Velcro ® mating elements 70, 72 are mated so as to initially maintain the encircled rib grid in a snug fit about the forearm of the wearer. (It is here noted that the flexible ribs 12 enable the grid to trace the configuration of the fracture site, even in the presence of tissue swelling, and thus allows the fracture site to be rigidly immobilized).

Figure 6:
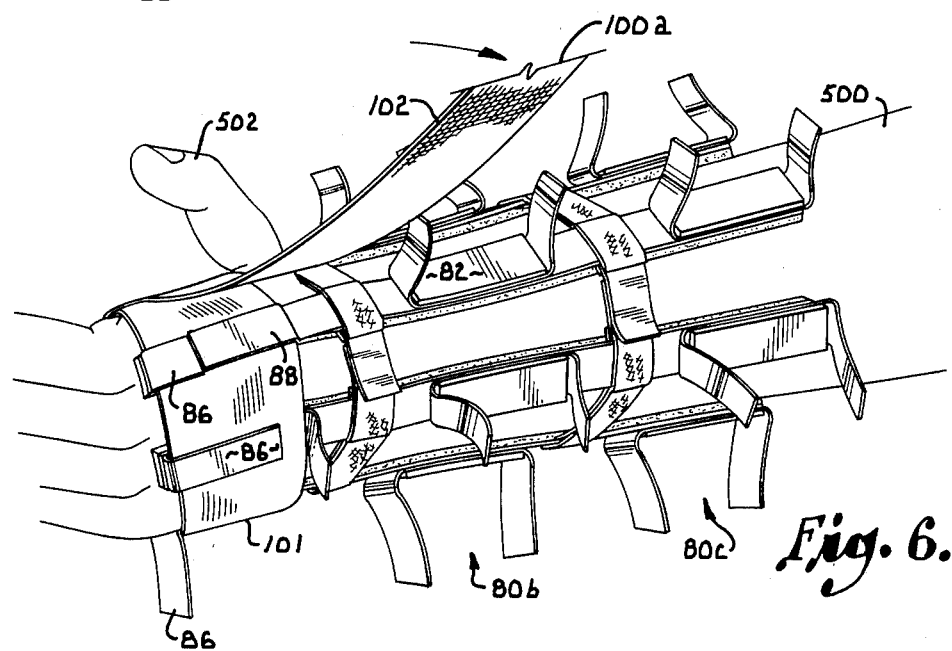
FIG. 6 is a view, as in FIG. 5, illustrating the initial placement of a ply of the first casting tape within the tape fasteners with the flaps of one tape fastener being shown in an overlapped position prior to the overlay of the second ply.
Figure 7:
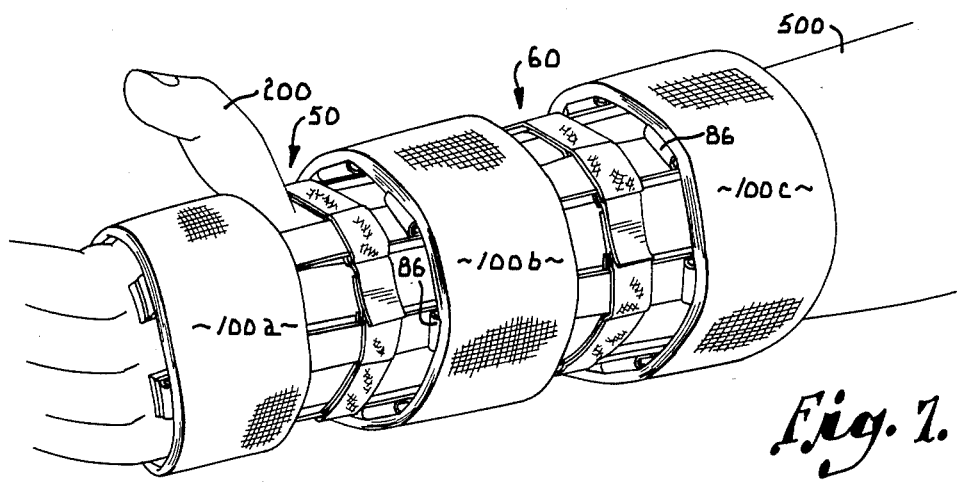
FIG. 7 illustrates the improved cast in a final immobilizing position with the first, second and third casting tapes being fully wound about the tape fasteners for subsequent drying and hardening in place.

Subsequently, as shown in FIG. 6, a water-activated, polyurethane casting tape 100a is preferably used and wound about the rib grid. Upon drying, the tapes 100a, 100b, 100c rigidify so as to more securely maintain the rib grid in place. The tape fasteners 80a, 80b, 80c present zones of reception to the doctor for the first ply of the respective casting tapes 100a, 100b, 100c. As such the first ply 101a of the casting tape 100a is wound about the rib array such as to overlay the laterally aligned bases 82 of each tape fastener. Once the first ply 101 is so wound, the tabs or flaps 86, 88 are folded one atop the other (FIG. 6) with the second ply (102, FIG. 6) of the casting tape 100a covering these overlapped tabs 86, 88. The moistened but still flexible casting tape 100a is then wound about the rib grid such that the successive plies are aligned one atop the other (FIGS. 6, 7). This same procedure is provided for the subsequent application of casting tapes 100b, 100c in the subsequent longitudinally displaced zones of reception as presented by tape fasteners 80b, 80c.

Once the tapes dry (FIG. 7) and rigidify, the fracture site is rendered immobile by the rib array/tape combination so as to enhance subsequent healing. The tape fasteners 80a, 80b, 80c not only present visual indicia for proper tape 100a, 100b, and 100c placement but also preclude undesirable shifting of the base ply of the casting tape during initial application and subsequent drying. Also, the laterally aligned bases 82 assist in displacing the tape 100 from the underlying skin during application and subsequent drying.

The utilization of the grid/lattice array in my cast 10 reduces the weight of the cast which delimits the interference of the cast with the normal daily activities of the wearer. The grid further allows sunshine and air to impinge upon the fracture site which precludes the maintenance of undesirable moisture in the fracture site. As such, the user may shower with the cast and the cast may be washed with assurance that the foam padding 16/moistened skin can be subsequently dried. Accordingly, the chances of cast deterioration, skin rashes, itching and the like are substantially lessened.

The use of the latticed cast and the presentation of spaces between the flexible ribs is believed to be effective in maintaining normal blood circulation through the fracture site so as to enhance healing. Also, the flexible ribs preclude the undesirable indention of the cast on the fracture site which may also interfere with blood circulation and pressure sores.

The use of the straps 50, 60, along with the tape fasteners 80a, 80b, 80c, allows my cast to be easily applied. The cast does not infringe with X-ray inspection and allows for a visual inspection of the fracture site along with application of medicines to the site area. Finally, the ability to view the fracture site enhances the easy removal of the cast after healing.

It is again noted that my improved cast has been above-described to a site specific area and should not be limited to such application thereto. Thus, the length or number of casting tapes 100 utilized may change according to the fracture to be immobilized.

Thus, it is to be understood that while certain forms of this invention have been illustrated and described, it is not limited thereto, except in so far as such limitations are included in the following claims.

Having thus described the invention, what is claimed as new and desired to be secured by Letters Patent is:

1. A cast for immobilizing a fracture site comprising:
   a plurality of elongated, laterally spaced-apart ribs for providing longitudinal support about said fracture site;
   means for maintaining said ribs in said spaced-apart relationship to present a grid of said ribs;
   fastener means on said rib grid for intially holding said grid in a desired position encircling said fracture site with the ribs disposed at circumferentially spaced intervals thereabout; and
   a plurality of initially flexible casting tapes for winding about said rib grid at selected, spaced-apart longitudinal positions therealong, said tapes rigidifying on said rib grid to maintain the same in said desired position encircling said fracture site, whereby said wound casting tapes further maintain said rib grid about said fracture site to provide longitudinal immobilzation of the same.

2. The apparatus as claimed in claim 1, wherein each of said ribs comprises:
   an enlongated face strip;

a strip of foam padding affixed to the inner side of said face strip, said padding contacting said skin of said fracture site.

3. The apparatus as claimed in claim 2, further comprising a plurality of base members each attached intermediate its opposed end portions to a respective face strip, said base members being longitudinally spaced and laterally interaligned to present zones of overlay for a first ply of each of said casting tapes wound about said rib grid, each of said base members having first and second flaps extending from its opposed end portions, said flaps being folded atop at least a first ply of said wound casting tapes and held in place by a successive ply of said wound casting tapes, said flaps holding said underlying plies of said casting tapes in place during drying.

4. The apparatus as claimed in claim 1 wherein said maintaining means is presented by at least one flexible strap traversing said spaced-apart ribs and affixed thereto, said strap having said fastener means thereon for holding said ribs about said fracture site.

5. The apparatus as claimed in claim 4 wherein said fastening means comprises complementary Velcro mating elements at the opposed end of each strap, whereupon said mating of said elements holds said strap about said fracture site and said ribs affixed thereto.

6. A cast for immobilizing a fracture site comprising:
a plurality of elongated, laterally spaced-apart ribs for providing longitudinal support about said fracture site, each of said ribs comprising an elongated face strip and a strip of foam padding affixed to the inner side of said fracture site;
means for maintaining said ribs in said spaced-apart relationship to present a grid of said ribs;
means for initially holding said rib grid in a desired position about said fracture site;
at least one initially flexible casting tape for winding about said rib grid at selected longitudinal positions theralong, said tape adapted to rigidify upon an initial moistening and subsequent drying;
means on said ribs for indicating said selected positions of said casting tape including a base member on each of said face strips, said base members being laterally interaligned to present zones of overlay for a first ply of said casting tape wound about said rib grid; and
a strip of flexible material interposed between each base member and its underlying face strip, each strip of material being relatively longer than the corresponding base member to present first and second flaps extending from opposed sides of the base member, said flaps being folded atop at least a first ply of said wound casting tape and held in place by a successive ply of said wound casting tape, said flaps holding said underlying plies of said casting tape in place during drying, whereby said wound casting tape further maintain said rib grid about said fracture site to provide immobilization of the same.

7. The apparatus as claimed in claim 6 wherein said maintaining means is presented by at least one flexible strap traversing said spaced-apart ribs and affixed thereto.

8. The apparatus as claimed in claim 7 wherein said holding means comprises complementary Velcro mating elements at the opposed ends of said strap, whereupon said mating of said elements holds said strap about said fracture site and said ribs affixed thereto.

9. A cast for immobilizing a fracture site comprising:
a plurality of laterally spaced-apart ribs for providing longitudinal support about said fracture site, each of said ribs comprising an elongated face strip and a strip of foam padding affixed to the inner side of said face strip, said padding contacting the skin of said fracture site;
means for maintaining said ribs in said spaced-apart relationship to present a grid of said ribs in a desired position about said fracture site;
at least one initially flexible casting tape for winding about said rib grid at selected longitudinal positions theralong, said tape adapted to rigidify upon an initial moistening and subsequent drying;
means on said ribs for indicating said selected positions of said casting tape including a base member on each of said face strips, said base members being laterally interaligned to present zones of overlay for a first ply of said casting tape wound about said rib grid;
a strip of flexible material interposed between each base member and its underlying face strip, each strip of material being relatively longer than the corresponding base member to present first and second flaps extending from opposed sides of the base member, said flaps being folded atop at least a first ply of said wound casting tape and held in place by a successive ply of said wound casting tape, said flaps holding said underlying plies of said casting tape in place during drying, whereby said wound casting tape further maintains said rib grid about said fracture site to provide longitudinal immobilization of the same.

10. The apparatus as claimed in claim 9 wherein said maintaining means is presented by at least one flexible strap traversing said spaced-apart ribs and affixed thereto, said strap having means thereon for fastening about said fracture site.

* * * * *